(12) United States Patent
Hansen

(10) Patent No.: US 8,158,151 B2
(45) Date of Patent: Apr. 17, 2012

(54) SOLVENT-ASSISTED LOADING OF THERAPEUTIC AGENTS

(75) Inventor: James G. Hansen, Coon Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2589 days.

(21) Appl. No.: 10/915,274

(22) Filed: Aug. 10, 2004

(65) Prior Publication Data

US 2006/0034931 A1 Feb. 16, 2006

(51) Int. Cl.
*A61K 9/14* (2006.01)
*B05D 1/04* (2006.01)
*A61L 27/00* (2006.01)
*A61L 31/00* (2006.01)

(52) U.S. Cl. .................... 424/486; 427/2.1; 427/475

(58) Field of Classification Search .................. None
See application file for complete search history.

(56) References Cited

U.S. PATENT DOCUMENTS

| | | | |
|---|---|---|---|
| 5,400,971 A | 3/1995 | Maugans et al. | 239/416.1 |
| 5,733,925 A | 3/1998 | Kunz et al. | 514/449 |
| RE36,378 E | 11/1999 | Mellette | 239/8 |
| 6,545,097 B2 | 4/2003 | Pinchuk et al. | 525/240 |
| 6,923,996 B2 * | 8/2005 | Epstein et al. | 427/2.24 |
| 2002/0107330 A1 * | 8/2002 | Pinchuk et al. | 525/242 |
| 2003/0054090 A1 | 3/2003 | Hansen | 427/2.1 |
| 2003/0077310 A1 | 4/2003 | Pathak et al. | 424/423 |
| 2003/0195610 A1 * | 10/2003 | Herrmann et al. | 623/1.15 |
| 2004/0059409 A1 | 3/2004 | Stenzel | 623/1.15 |
| 2004/0234748 A1 | 11/2004 | Stenzel | 428/327 |
| 2005/0175772 A1 * | 8/2005 | Worsham et al. | 427/165 |

FOREIGN PATENT DOCUMENTS

| | | |
|---|---|---|
| EP | 0 850 651 A2 * | 7/1998 |
| WO | WO 2004/014448 A1 | 2/2004 |

OTHER PUBLICATIONS

Websearch for term "solid aerosol"; http://medical-dictionary.thefreedictionary.com/Solid+aerosol.*
Rentz, O., et al. "Best Available Techniques (BAT) for the Paint-and-Adhesive Application in Germany", vol. 1: Paint Application, http://www.umweltdaten.de/nfp-bat-e/vol1paint.pdf, Aug. 2002, Cover Sheet, Table of Contents, and pp. 296-304.
Waters, Jean S. et al., "Environmentally conscious painting," Kansas Small Business Environmental Assistance Program, Jun. 1996, Cover Sheet, Table of Contents, and pp. 1-31.

* cited by examiner

*Primary Examiner* — Robert A Wax
*Assistant Examiner* — Jeffrey T Palenik
(74) *Attorney, Agent, or Firm* — Mayer & Williams PC; David B. Bonham; Keum J. Park

(57) ABSTRACT

Methods are provided for loading polymeric regions of medical devices with therapeutic agents. In these methods, a polymeric region of a medical device is first pretreated with a solvent system. Subsequently, therapeutic-agent-containing particles are impacted into the pretreated polymeric region at a velocity that is effective to at least partially embed the particles within the pretreated polymeric region. The pretreatment step parameters (e.g., the particular solvent system employed, amount of time that the solvent system contacts the polymeric region, etc.) are typically selected such that the surface tack of the polymeric region is increased. Consequently, the depth, the amount, or both the depth and the amount of the particles that become at least partially embedded in the polymeric region is/are typically increased, relative to what would be achieved in the absence of the pretreatment step. Also provided are medical devices made by such methods.

30 Claims, No Drawings

SOLVENT-ASSISTED LOADING OF THERAPEUTIC AGENTS

FIELD OF THE INVENTION

The present invention relates to medical devices which contain polymeric regions for release of therapeutic agents, and to methods of forming the same.

BACKGROUND OF THE INVENTION

Numerous polymer-based medical devices have been developed for the delivery of therapeutic agents to the body. In accordance with some delivery strategies, a therapeutic agent is provided within a polymeric region of a medical device (e.g., a polymeric layer overlying a medical device substrate). Once the medical device is placed at the desired location within a patient, the therapeutic agent is locally released from the medical device to achieve a site-specific effect. As a result of this localized delivery, significantly lower doses therapeutic agent are used than would otherwise be required in connection with a systemic administration scheme (e.g., administration via an oral or parenteral route). In using lower doses, unwanted or even toxic side effects of significant systemic concentrations of therapeutic agent can often be avoided.

Methods have been described for loading polymeric regions of medical devices with therapeutic agents. For example, U.S. Pat. No. 6,545,097 to Pinchuk et al., which is incorporated herein by reference in its entirety, describes a method in which a therapeutic agent is dissolved in a solvent, and the resulting solution contacted with a polymeric region of a medical device, such that the therapeutic agent is loaded (e.g., by leaching/diffusion) into the same. For this purpose, the polymeric region can be immersed or dipped into the solution, or the solution can be applied to the polymeric region, for example, by spraying. The polymeric region can subsequently be dried, with therapeutic agent remaining therein.

Highly solvented mixtures have been used for many years in the automotive industry. For example, processes are known in which a solvent-only spray is directed to the edges of an area that has been repainted during the course of automotive repair. As a result, the paint is resolvated in place and the spray edges are blended with the prior coat, thus reducing or eliminating the need from polishing the edges. As another example, it is desirable in the automotive industry to cause metal flakes to stand on edge, thereby achieving the greatest light reflectance from the flakes. To achieve this goal, techniques are sometimes used in which the surface of a freshly painted panel is first softened using a solvent-only spray, after which a mixture of metal flakes and solvent is sprayed at high velocity onto the softened panel. Surface wetness can be controlled by altering the distance from the sprayer to the panel, which is an important process parameter, as the metal flake will not stand on edge if the surface is too wet and will not properly penetrate if the surface is too dry. The surface is then allowed to dry for a short period, securing the metal flakes in place. The surface then receives a so-called "clear coat" to protect the metal flakes from oxidation and to increase surface durability.

SUMMARY OF THE INVENTION

In accordance with certain aspects of the present invention, methods are provided for loading a polymeric region of a medical device with a therapeutic agent. These methods comprise the following steps: (a) pretreating the polymeric region of the medical device with a solvent system and (b) impacting therapeutic-agent-containing particles into the pretreated polymeric region at a velocity that is effective to at least partially embed the particles within the pretreated polymeric region.

Other aspects of the present invention are directed to medical devices formed by these methods.

An advantage of the present invention is that a method is provided by which therapeutic agent can be efficiently introduced into the surface of a pre-existing polymeric region.

In certain embodiments, the polymeric regions will comprise polymers with which the automotive industry has significant experience, for example, acrylic and urethane polymers. These embodiments are advantageous in that solvent systems are already well-established and characterized, which are effective for partially solvating and softening such polymers.

These and other aspects, embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of various different aspects and embodiments of the invention. The detailed description that follows is intended to illustrate but not limit the invention. The scope of the invention is defined by the appended claims.

According to one aspect of the invention, methods are provided for loading polymeric regions of medical devices with therapeutic agents. In these methods, the polymeric region of the medical device is first pretreated with a solvent system. Subsequently, therapeutic-agent-containing particles are impacted into the pretreated polymeric region at a velocity that is effective to at least partially embed the particles within the pretreated polymeric region. The pretreatment step parameters (e.g., the particular solvent system employed, the amount of time that the solvent system contacts the polymeric region, etc.) are selected such that the depth, the amount, or both the depth and the amount, of the particles that become at least partially embedded in the polymeric region is/are optimized, and these parameters are generally increased, relative to what would be achieved in the absence of the pretreatment step.

Using such methods, a wide range of medical devices can be loaded with therapeutic agent. Medical devices for use in conjunction with the present invention include essentially any medical device for which controlled release of a therapeutic agent is desired. Examples of medical devices include implantable or insertable medical devices, for example, catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, biopsy devices, and any coated substrate (which can comprise, for example, glass, metal, polymer, ceramic and combinations thereof) that is implanted or inserted into the body and from which therapeutic agent is released. Examples of medical devices further include patches for delivery of therapeutic agent to intact skin and broken skin (including wounds); sutures, suture anchors, anastomosis clips and rings, tissue staples and ligating clips at surgical sites; orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery; and tissue engineering scaffolds for cartilage, bone, skin and other in vivo tissue regeneration.

As used herein, a "polymeric region" is a region of material that contains at least one polymer. The polymeric regions of the invention typically contain 75 wt % or more polymer, more typically 90 wt % or more, 95 wt % or more, or even at 99% wt % or more polymer.

The polymeric region can correspond to the entire device (e.g., an entire stent), or to one or more portions of the medical device For example, the polymeric region(s) can correspond to one or more components of the medical device (e.g., one or more stent struts). As another example, the polymeric regions (s) can be disposed over an underlying medical device substrate, for example, in the form of one or more coating regions, which can cover all or only a portion of the underlying medical device substrate. Substrates include, for example, metallic, ceramic and polymeric substrates.

In some embodiments, the therapeutic agent is introduced into the polymeric region, and the polymeric region subsequently associated with (e.g., attached to) a medical device. In some embodiments, the polymeric region is already associated with a medical device at the time of therapeutic agent introduction.

Depending on the nature of the therapeutic-agent-containing region(s) provided, the therapeutic agent may ultimately be released from the medical device to the subject by any of a number of mechanisms including diffusion, biodisintegration and/or other release mechanisms. Preferred subjects (also referred to as patients) are mammalian subjects and more preferably human subjects.

The polymeric regions for use in conjunction with the present invention can comprise a wide range of polymers. For example, the polymers may be homopolymers or copolymers (including alternating, random, statistical, gradient and block copolymers), they may be cyclic, linear or branched (e.g., the polymers may have star, comb or dendritic architecture), they may be natural or synthetic, and so forth.

Polymers for use in the polymeric regions may be selected, for example, from solvatable members of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polyamide polymers and copolymers including nylon 6,6, nylon 12, polycaprolactams and polyacrylamides; resins including alkyd resins, phenolic resins, urea resins, melamine resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers; vinyl aromatic polymers and copolymers such as polystyrenes, styrene-maleic anhydride copolymers, vinyl-aromatic-olefin copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk et al.), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly (caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as derivatives, and additional blends and copolymers of the above.

Polymeric regions can be formed using a variety of processing techniques, including solvent-based techniques and thermoplastic-based techniques (where the polymer has thermoplastic characteristics). In thermoplastic-based processing, the polymer is heated until it forms a polymer melt, whereupon the polymeric region is formed from the melt. Examples of thermoplastic processing techniques include compression molding, injection molding, blow molding, spinning, vacuum forming and calendaring, and extrusion. In solvent-based processing, the polymer is first dissolved in a solvent system and the resulting solution is subsequently used to form the polymeric region. Preferred techniques of this nature include solvent casting, spin coating, web coating, spraying, dipping, fiber forming, ink jet techniques, electrostatic spray techniques, and the like.

As previously indicated, once an appropriate polymeric region is provided, a solvent system is brought into contact with the same. Contact between the polymeric region and solvent may occur via a variety of techniques, including spraying techniques, roll and brush coating techniques, spin coating techniques, dipping techniques, web coating techniques, and so forth. A typical contact method is spraying. Various types of spraying techniques are described below.

As used herein, a "solvent system" is a liquid that contains at least one solvent species. The solvent system typically contains 90 wt % or more of the solvent species, more typically 95 wt % or more, 99 wt % or more, or even at 99.9% wt % or more of the solvent species.

Subsequent to pretreatment of the polymeric region with the solvent system, the polymeric region is impacted with therapeutic-agent-containing particles, which are traveling at a velocity that is effective to at least partially embed the particles within the polymeric region. The pretreatment step parameters (e.g., the particular solvent system employed, the amount of time that the solvent system contacts the polymeric region prior to particle impact, etc.) are typically selected such that the depth, the amount, or both the depth and the amount of particles becoming at least partially embedded in the polymeric region is increased, when compared to impacting the polymeric region with the therapeutic-agent-containing particles in the absence of the pretreatment step. Whether or not this outcome has been achieved can be readily determined by those of ordinary skill in the art. For example, the distribution of the therapeutic-agent-containing particles within the polymeric region as a function of depth can be readily analyzed, for instance, by well known analytical techniques such as microscopic techniques, atomic force spectroscopy, and kinetic drug release measurements.

The time required for the solvent system to exert a measurable effect upon the polymeric region can vary significantly, but the solvent system is typically selected to provide a change in property within a matter of a few minutes (e.g., less than 10 minutes), and more typically within a minute or less, for example, to minimize solvent evaporation.

An increase in the depth and/or or amount of particles that become at least partially embedded in the polymeric region will typically be accompanied by an increase in the surface tack of the polymeric region and may also be accompanied, for example, by softening and/or swelling of the polymeric region surface.

Using the above criteria as a guide, solvent species for use in the solvent systems of the present invention can be readily selected, for example, from any combination of one or more of the following solvents: (a) water, (b) alkanes such as ethane, hexane, octane, cyclohexane, heptane, isohexane, butane, pentane, isopentane, etc., (c) aromatic species such as benzene, toluene, xylene(s), naphthalene, etc., (d) halohydrocarbons including (i) chlorohyhdrocarbons such as chloroform, methyl chloride, dichloromethane, 1,1-dichloroethylene, ethylene dichloride, etc. (ii) fluorinated halogenated species such as chlorodiflouoromethane, dichlorofluoromethane, etc. and (iii) other halohydrocarbons such as ethyl bromide, ethylidene bromide, ethylene dibromide, tribromomethane, etc. (e) acid aldehydes/anhydrides such as acetaldehyde, furfural, acetic anhydride, etc. (f) alcohols including (i) phenols such as phenol, 1,3-benzenediol, m-cresol, o-methoxyphenol, etc., (ii) polyhydric alcohols such as ethylene glycol, glycerol, propylene glycol, 1,3-butanediol, etc. and (iii) other alcohols such as methanol, ethanol, 1-propanol, 2-propanol, 3-chloropropanol, etc., (g) ethers such as, epichlorohydrin, furan, 1,4-dioxane, diethyl ether, dimethyl ether, tetrahydrofuran, etc. (h) ketones, such as acetone, cylohexanone, diethyl ketone, methyl ethyl ketone, etc., (i) acids such as formic acid, acetic acid, benzoic acid, etc., (j) esters/acetates such as ethylene carbonate, ethyl acetate, ethyl formate, n-butyl acetate, dimethyl phthalate, dibutyl phthalate, diethyl phthalate, n-propyl acetate, etc., (k) nitrogen compounds such as acetonitrile, acrylonitrile, n,n-dimethylformamide, etc., and (l) sulfur compounds such as carbon disulfide, dimethylsulfoxide, etc.

As noted above, once the polymeric region has been pretreated with the solvent system, particles that comprise the therapeutic agent are impacted into the pretreated polymeric region at a velocity effective to at least partially embed the particles within the pretreated polymeric region.

The particles become bonded with the polymeric region upon removal of residual solvent species, e.g., by natural evaporation, by heating, by application of a vacuum, by heating under vacuum, and so forth.

The therapeutic-agent-containing particles can be impacted, for example, in dry powder form or in association with a liquid containing one or more liquid species. The particles can, for example, consist essentially of the therapeutic agent, or they can contain the therapeutic agent and one or more pharmaceutically acceptable agents. Examples of pharmaceutically acceptable agents include, for example, excipients such as binders, fillers (diluents), buffering agents, osmolality adjusting substances, and so forth. Particle sizes typically range from 5 to 1000 nm, more typically from 20 to 25 nm.

Where the therapeutic-agent-containing particles are provided in association with one or more liquid species, the liquid species may be the same as, or different from, the species making up the solvent system that is used in the pretreatment step. In some embodiments (including embodiments where the liquid species are the same as those used in the prtetreatment step) the liquid species are selected, at least in part, based on their ability to enhance the penetration of the therapeutic-agent-containing particles into the polymeric region upon impact. The ratio of liquid to solids in these and other embodiments is quite high, for example, exceeding 20 to 1, 100 to 1 or even exceeding 1000 to 1 in some instances.

The method by which the therapeutic-agent-containing particles are impacted with the pretreated polymeric region will depend, for example, upon the form of the composition that contains the particles. For example, where the therapeutic-agent-containing particles are provided in powder form, apparatuses akin to sand blasting apparatuses can be employed for particle impact.

As another example, where the therapeutic-agent-containing particles are provided in association with one or more liquid species, various spraying systems can be employed for particle impact. Examples of spraying systems include, for example, conventional air spray systems, high volume low pressure (HVLP) spray systems, airless spray systems, air-assisted airless systems, and electrostatic systems. Surface wetness can be controlled by altering the distance from the sprayer to the polymeric region Conventional air spray systems are capable of delivering atomized spray particles at relatively high velocity. In these devices, air delivered to the spray head has a relatively high pressure and volume. As the air exits the spray head, it atomizes a stream of fluid into a conically-shaped spray, which may be flattened into a fan-shaped pattern by opposing side port air jets. When the high pressure and high volume air exits the spray head, it expands and imparts a relatively high velocity to the spray particles.

With airless spray systems, fluid is hydraulically forced through a specially shaped orifice at pressures on the order of 500-4500 psi, which causes the fluid to be emitted in an unstable thin film that interacts with atmospheric air and breaks up into an atomized spray at its forward edge. Airless spray systems have a somewhat higher transfer efficiency than conventional air spray, but they typically develop spray particles that have a lower velocity than conventional air spray guns.

Air-assisted airless systems are also available, which utilizes both airless and air atomization. Fluid is supplied to a specially shaped orifice at hydraulic pressures less than those normally encountered in purely airless systems, usually on the order of 300-1,000 psi. This causes the material to be atomized into a spray, but the degree of atomization is not as satisfactory as that obtained with conventional airless or air spray guns. To improve atomization, an air-assist is applied to the spray pattern, enhancing the atomization process. The transfer efficiency of air-assisted airless systems is greater than those of conventional airless or air spray systems.

High volume low pressure (HVLP) spray systems are also available which have high transfer efficiency. These systems utilize air to atomize a stream of fluid, but at the spray head the air has a relatively high flow rate and a relatively low delivery pressure usually less than 15 psi. The high volume and low pressure of the air results in an increased percentage of the spray particles striking and adhering to the target. An exemplary high volume low pressure air spray gun is described in U.S. Pat. No. Re. 36,378, the disclosure of which is hereby incorporated by reference in its entirety.

Transfer efficiency and spray velocity can also be enhanced by employing electrostatic or electrohydrodynamic spraying systems, which typically have some mechanism for applying a charge to the fluid being sprayed.

For example, in some apparatuses, charging is accomplished by an electrode connected to a high voltage supply and placed in close proximity to, or in contact with, the fluid, either just prior or close to its point of atomization. Atomization can proceed, for example, using one of the above-described techniques.

In rotary atomization apparatuses, which rely on electrostatic charge to guide the fluid to the device, the rotary atomizer is ordinarily made of a conductive material and connected to the power supply, so the atomizer itself is the electrode.

In typical electrohydrodynamic spray systems, fluid is delivered to a nozzle maintained at high electric potential, whereupon the fluid is aerosolized. One type of nozzle used in electrohydrodynamic spray systems is an electrically conductive capillary tube. By applying an electric potential to the capillary tube, fluid emerging from the tip of the tube is charged. The electrical forces exerted on the emerging fluid, balanced with the surface tension of the fluid, causes the fluid to emerge from the capillary in the shape of a cone and/or jet. Beneficially, the charge on the fluid overcomes the surface tension and at the tip of the cone, and a thin jet of fluid forms, which subsequently rapidly separates a short distance beyond the tip into an aerosol. Studies have shown that this aerosol has a fairly uniform droplet size and a high velocity near the tip.

In many embodiments, the therapeutic-agent-containing particles are associated with one or more liquid species prior to introduction into the spraying system, for example, by providing a suspension of therapeutic-agent-containing particles in one or more liquid species. In these embodiments, it is generally preferred that the therapeutic-agent-containing particles be substantially insoluble in the liquid species.

Alternatively, the therapeutic-agent-containing particles can be admixed with a liquid that contains one or more liquid species within the spray apparatus. Spray guns are available for mixing plural components at the time of spraying. For example, U.S. Pat. No. 5,400,971, the entire disclosure of which is hereby incorporated by reference, describes a spray gun having one or more injector assemblies mounted for injecting a catalyst into a main component stream at the most forward position of the spray gun. This or a similar apparatus can be modified such that the therapeutic-agent-containing particles are combined with a main component stream at the point of emergence from the spray gun. In such embodiments, the therapeutic-agent-containing particles may be suspended in air, or they may be provided within a liquid, whose composition may be the same as or different from the composition of the liquid in the main component stream. For example, this may allow for the therapeutic-agent-containing particles to be suspended in a liquid in which they have low solubility and subsequently combined with another stream containing a liquid which is effective to soften the polymeric region, but which would result in unacceptably high dissolution of the therapeutic-agent-containing particles, given sufficient exposure time.

In some embodiments, the therapeutic-agent-containing particles are impacted with the pretreated polymeric region at high velocities. Methods are known by which velocity can be readily measured, including phase Doppler anemometry. Using phase Doppler anemometry, the size and velocity of particles passing through a detection region, which is established by the intersection of two laser beams, can be measured. The particles passing through the detection region cause light to be scattered, which is received by a photodetector and analyzed. Phase Doppler particle analyzers are available, for example, from Aerometrics Inc., Sunnyvale California.

"Drugs," "therapeutic agents," "pharmaceutically active agents," "pharmaceutically active materials," and other related terms may be used interchangeably herein. These terms include genetic therapeutic agents, non-genetic therapeutic agents and cells. Therapeutic agents may be used singly or in combination in the medical devices of the present invention, within a single population of particles or multiple populations of particles. Therapeutic agents can be selected from members of those therapeutic agents listed below, and should be substantially compatible with the selected solvent (s), so as to avoid unacceptably high losses in the biological activity of the therapeutic agent Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o)agents that interfere with endogenous vasoactive mechanisms; (p) inhibitors of leukocyte recruitment, such as monoclonal antibodies; (q) cytokines; (r) hormones and (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin.

Preferred non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel and Ridogrel.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP) and SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical devices of the present invention, with the therapeutically effective amount being readily determined by those of ordinary skill in the art and ultimately depending, for example, upon the condition to be treated, the age, sex and condition of the patient, the nature of the therapeutic agent, the nature of the polymeric region(s), the nature of the medical device, and so forth.

EXAMPLE

A medical device (e.g., a stent) containing a polymeric region (e.g., a polymeric coating) which consists essentially of one or more polymers that are water-insoluble and non-water-swellable (e.g., vinyl-aromatic-olefin copolymers such as SIBS, or polycarbonate based polyurethane copolymers such as Bionate®) is pretreated by exposing it to a non-aqueous solvent system (e.g., via spraying) that consists essentially of one or more non-aqueous solvent species, such as those listed above, for example, tetrahydrofuran, toluene, dimethyl formamide, methyl ethyl ketone and combinations of the same. Subsequently, an aerosol of therapeutic agent particles (e.g., paclitaxel particles) is combined with a liquid stream (e.g., a stream having the same composition as the pretreatment solvent system) in a multi-component spray gun like that discussed above, and sprayed into the surface of the pretreated polymeric region, whereupon the therapeutic agent particles become at least partially embedded in the polymeric region. The particles become bonded with the polymeric region upon removal of the solvent species.

Although various aspects and embodiments are specifically described herein, it will be appreciated that modifications and variations of the present invention are covered by the above teachings and are within the purview of the appended claims without departing from the spirit and intended scope of the invention.

The invention claimed is:

1. A method for loading a polymeric region of a medical device with a therapeutic agent, said method comprising:
   pretreating the polymeric region of the medical device with a solvent system that is effective to increase the surface tack of the polymeric region; and
   impacting particles comprising the therapeutic agent into the pretreated polymeric region at a velocity that is effective to at least partially embed the particles within the pretreated polymeric region, wherein said particles are impacted in dry powder form.

2. The method of claim 1, wherein said medical device is selected from a guide wire, a balloon, a vena cava filter, a stent, a stent graft, a vascular graft, a cerebral aneurysm filler coil, a myocardial plug, a heart valve, a vascular valve.

3. The method of claim 1, wherein one or more polymers comprise at least 95 wt % of the polymeric region.

4. The method of claim 1, wherein said polymeric region comprises two or more polymers, each having different monomeric constituents.

5. The method of claim 1, wherein said polymeric region comprises a copolymer that comprises olefin and vinyl aromatic monomeric constituents.

6. The method of claim 1, wherein said polymeric region comprises a poly(olefin)-poly(vinyl aromatic) block copolymer.

7. The method of claim 1, wherein said polymeric region comprises a poly(isobutylene)-polystyrene block copolymer.

8. The method of claim 1, wherein said polymeric region comprises a polyurethane.

9. The method of claim 1, wherein said polymeric region comprises a polycarbonate-based polyurethane copolymer.

10. The method of claim 1, wherein said polymeric region comprises a polyisobutylene block copolymer.

11. The method of claim 1, wherein said polymeric region is a coating on an underlying medical device substrate.

12. The method of claim 1, wherein said solvent system comprises two or more solvent species.

13. The method of claim 1, wherein one or more solvent species comprise at least 95 wt % of the solvent system.

14. The method of claim 1, wherein said solvent system comprises a solvent species selected from toluene, methyl ethyl ketone, tetrahydrofuran, n,n-dimethyl formamide, and combinations thereof.

15. The method of claim 1, wherein said particles comprise a therapeutic agent selected from paclitaxel, heparin and combinations thereof.

16. The method of claim 1, wherein said particles further comprise a pharmaceutically acceptable excipient.

17. The method of claim 1, wherein said particles consist essentially of said therapeutic agent.

18. The method of claim 1, wherein a gaseous stream comprising said particles impacts said polymeric region.

19. The method of claim 18, wherein said particles are present in said gaseous stream as a solid aerosol.

20. The method of claim 18, wherein said particles are present in said gaseous stream within an aerosolized liquid.

21. A medical device formed by the method of claim 1.

22. A method for loading a polymeric region of a medical device with paclitaxel, said method comprising:
  pretreating the polymeric region of the medical device with a solvent system that is effective to increase the surface tack of the polymeric region, said polymeric region comprising a polyisobutylene block copolymer; and
  impacting particles comprising paclitaxel into the pretreated polymeric region at a velocity that is effective to at least partially embed the particles within the pretreated polymeric region, wherein said particles are impacted in dry powder form.

23. The method of claim 1, wherein said particles are sprayed onto said pretreated polymeric region.

24. The method of claim 23, wherein said particles are sprayed using a spray system selected from air spray systems, high volume low pressure (HVLP) spray systems, airless spray systems, air-assisted airless systems, and electrostatic systems.

25. The method of claim 23, wherein a stream of said particles is admixed with a stream of liquid comprising one or more liquid species upon emerging from a spray apparatus.

26. The method of claim 23, wherein said particles are suspended in a gas.

27. The method of claim 25, wherein said particles are suspended in a liquid.

28. The method of claim 1, wherein said polymeric region does not contain a therapeutic agent.

29. The method of claim 1, wherein said solvent system comprises 99.9 wt % or more of one or more solvent species.

30. A method for loading a polymeric region of a medical device with a therapeutic agent, said method comprising:
  pretreating the polymeric region of the medical device with a solvent system that is effective to increase the surface tack of the polymeric region, wherein one or more solvent species constitute at least 99 wt % of the solvent system; and
  impacting particles comprising the therapeutic agent into the treated polymeric region at a velocity that is effective to at least partially embed the particles within the pretreated polymeric region, said impacting particles being in dry powder form.

* * * * *